United States Patent [19]

Uggeri et al.

[11] Patent Number: 4,620,031

[45] Date of Patent: Oct. 28, 1986

[54] PROCESS FOR PREPARING ALPHA-ARYL-ALKANOIC ACIDS

[75] Inventors: Fulvio Uggeri, Codogno; Graziano Castaldi, Briona; Claudio Giordano, Vicenza, all of Italy

[73] Assignee: Zambon S.p.A., Vicenza, Italy

[21] Appl. No.: 697,449

[22] Filed: Feb. 1, 1985

[30] Foreign Application Priority Data

Feb. 3, 1984 [IT] Italy ............................. 19434 A/84

[51] Int. Cl.⁴ ............................................. C07C 63/36
[52] U.S. Cl. ..................................... 562/466; 549/79; 562/465; 562/496
[58] Field of Search ............... 562/466, 465, 496, 466; 549/79

[56] References Cited

U.S. PATENT DOCUMENTS 4,542,237 9/1985 Schloemer ........................ 562/466

Primary Examiner—Paul J. Killos
Attorney, Agent, or Firm—Cushman, Darby & Cushman

[57] ABSTRACT

Alpha-alkyl-alkanoic acids are prepared by heating at boiling temperature a mixture of an alpha-halogen-alkyl-arylketone in a saturated aliphatic diol or in a mixture of saturated aliphatic diols in the presence of a Broensted's acid and by successively alkalifying the reaction mixture.

5 Claims, No Drawings

PROCESS FOR PREPARING ALPHA-ARYL-ALKANOIC ACIDS

The present invention relates to a process for preparing alpha-aryl-alkanoic acids.

More precisely, it relates to a process extremely simple and easily accomplishable on an industrial scale, allowing the alpha-aryl-alkanoic acids to be prepared starting from the corresponding alpha-halogen-alkyl-aryl-ketones, wherein the halogen is preferably chlorine or bromine.

In particular, the process consists in heating a mixture of an alpha-halogen-alkyl-arylketone in a saturated aliphatic diol or in a mixture of saturated aliphatic diols in the presence of a Broensted's acid, and in subsequently making alkaline the reaction mixture.

Suitable saturated aliphatic diols are straight- or branched-chain diols of from 2 to 10 carbon atoms, such as ethylene glycol, propylene glycol, 2,2-dimethyl-1,3-diol, 1,4-butanediol and 1,10-decanediol.

The reaction is preferably carried out at the boiling temperature of the reaction mixture, and the water being formed is distilled off.

The addition of the base is carried out at a temperature comprised within the range of from room temperature to 100° C., and said temperature must be high enough, so as to allow reaction times to be reduced, but not such as to cause byproducts to be formed; the Applicants prefer to operate at 60°–100° C. for 3 to 7 hours, and to use an inorganic base. Examples of suitable inorganic bases are the hydroxides of alkaline or alkaline-earth metals. After cooling, the alpha-aryl-alkanoic acid is isolated by means of conventional techniques, such as by extraction with suitable organic solvents, e.g. with methylene chloride.

Also the alpha-bromo- or -chloro-alkyl-arylketone used as the starting material is easily prepared by means of known techniques, such as the Friedel-Crafts reaction. It is thus evident that the process according to the present invention allows the desired acid to be prepared by means of only two steps easily accomplishable on an industrial scale.

Examples of alpha-aryl-alkanoic acids which can be prepared by means of the process according to the present invention are Alclofenac, Benoxaprofen, Carprofen, Diclofenac, Fenclofenac, Fenoprofen, Fentiazac, Flurbiprofen, Indoprofen, Ibuprofen, Isoprofen, Ketoprofen, Naproxen, Pirprofen, Surprofen, Tolmetin, Xenbucin, and similar compounds. Most of them are largely used in the medical field, thanks to their anti-inflammatory, analgesic and antipyretic properties.

Preferred alpha-aryl-alkanoic acids according to the present invention are those of formula

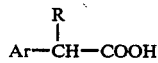

wherein

Ar is (a) a phenyl substituted with one or two halogen(s), $C_{1-4}$-alkyl, $C_{1-4}$-alkoxy, $C_{2-4}$-alkenyloxy, phenyl, phenoxy, dichlorophenoxy, dichloroanilino, benzoyl, indolinyl, dihydropyrrolyl, thenoyl; (b) a naphthyl substituted with one or two halogen(s) or $C_{1-4}$-alkoxyl; (c) a pyrryl substituted with one or two $C_{1-4}$-alkyl(s) and $C_{1-4}$-akylphenyl(s); (d) chlorocarbazolyl; (e) benzoxazolyl substituted with a chlorophenyl radical; (f) thyazolyl substituted with one or two phenyl(s) or chlorophenyls; and (g) thienyl;

R is either hydrogen or methyl.

The following Examples shall illustrate the present invention, however in no way being limitative thereof.

EXAMPLE 1

Preparation of 2-(6'-methoxy-2'-naphthyl)-propionic acid (a) To a mixture of 2-bromo-1-(6'-methoxy-2'-naphthyl)-propan-1-one (14.65 g; 50 mmole), ethylene glycol (62 g) and 2,2-dimethyl-1,3-propanediol (240 g) thermostatically kept at 140° C., p-toluenesulphonic acid (0.95 g; 5 mmole) is added.

The mixture is kept at 140° C. for 8,5 hours, a water-diols mixture being vacuum (80 mmHg) distilled. To the reaction mixture, cooled to 95° C., a 4% aqueous solution of NaOH (100 ml) is added, and the mixture is kept at the temperature said for 5 hours.

After cooling to room temperature, the reaction mixture is poured into water (350 ml) and extracted with methylene chloride (3×200 ml).

The organic extracts are washed with a 0.1N aqueous solution of hydrochloric acid (5×200 ml), and are then extracted with 10% aqueous sodium bicarbonate (3×200 ml). The aqueous phase is treated with charcoal (1.5 g) at 0° C. for 30 minutes, filtered on celite, made acid with concentrated hydrochloric acid and extracted with methylene chloride (3×200 ml). The combined organic extracts are washed with water (200 ml), dried on sodium sulphate and evaporated in vacuo.

Crude 2-(6'-methoxy-2'-naphthyl)-propionic acid (8 g) is obtained, having a gas-chromatographic assay value of 80% (NMR assay value of 90%) (yield, referred to the bromoketone, of 56%).

(b) A mixture of 2-bromo-1-(6'-methoxy-2'-naphthyl)-propan-1-one (14.65 g; 50 mmole), ethylene glycol (56 g), 2,2-dimethyl-1,3-propanediol (220 g) and p-toluenesulphonic acid (0.95 g; 5 mmole) is heated at 140° C. for 7 hours.

The mixture is cooled to 95° C., to is sodium hydroxide (4 g) and water (75 ml) is added, and it is kept at the temperature said for 6 hours.

The mixture is then processed as described under preceding (a) point.

Crude 2-(6'-methoxy-2'-naphthyl)-propionic acid (6,3 g) is obtained, whose assay value, determined by GLC, appears to be of 58% (yield of 32%).

(c) A mixture of 2-bromo-1-(6'-methoxy-2'-naphthyl)-propan-1-one (14.65 g; 50 mmole), ethylene glycol (56 g), 2,2-dimethyl-1,3-propanediol (220 g) and p-toluenesulphonic acid (0,95 g; 5 mmole) is heated at 125°–130° C. for 10 hours, while vacuum distilling off from it (40–50 mmHg) a mixture of water and diols, and reintegrating its volume by means of periodical additions of a mixture of ethylene glycol and 2,2-dimethyl-1,3-propanediol (weight ratio 1:4).

The mixture is cooled to 95° C., to it sodium hydroxide (4 g) and water (50 ml) is added, and it is then kept at the temperature said for 3 hours.

The mixture is then processed as described under preceding (a) point.

Crude 2-(6'-methoxy-2'-naphthyl)-propionic acid is so obtained (10.2 g), having a gas-chromatographic assay value of 81% (yield of 72%), melting point 154°–155° C.

EXAMPLE 2

Preparation of 2-(4'-methoxyphenyl)-propionic acid

A mixture of 1-(4'-methoxyphenyl)-2-bromo-1-propanone (24,3 g; 0.1 mole), p-toluenesulphonic acid (1,9 g; 0,01 mole) and ethylene glycol (750 ml) is heated at 115° C. under vacuum (40 mmHg) for three hours, while distilling off a mixture of glycol and water. To the mixture cooled to 60° C., neutralized by means of sodium methoxide (0.6 g; 0.011 mole), potassium acetate (11,77 g; 0,12 mole) is added, and the mixture is heated at 130° C. for 6 hours. The mixture is then cooled to 90° C., to it 40%-concentrated potassium hydroxide (30 ml) is added, and the mixture is kept at the temperature said for 5 hours. After cooling to room temperature, the reaction mixture is poured into water (200 ml) and extracted with methylene chloride (2×250 ml). The aqueous phase is then made acid by means of concentrated hydrochloric acid, and extracted with methylene chloride (4×250 ml). The methylene chloride phase is washed with water (4×500 ml), separated and evaporated under vacuum. The residual oil is dissolved in a 10% solution of sodium bicarbonate (500 g), treated with charcoal (1 g) and filtered on celite. The so-obtained clear solution is cooled to 0° C. and made acid to pH 1 by means of concentrated HCl. 2-(4'-Methoxyphenyl)-propionic acid precipitates (7 g; 0,038 mole). Yield of 38%; melting point 54°-55° C.

EXAMPLE 3

Preparation of 2-(6'-methoxy-2'-naphthyl)-propionic acid

A mixture of 2-bromo-1-(6'-methoxy-2'-naphthyl)-propan-1-one (29.35 g; 0.1 mole), p-toluenesulphonic acid (1.9 g; 0.01 mole) and ethylene glycol (750 ml) is heated at 115° C. under vacuum (40 mmHg) for 3 hours, while distilling off a mixture of glycol and water.

To the mixture, cooled to 60° C. and neutralized by means of sodium methoxide (0.6 g; 0.011 mole), potassium acetate (12 g; 0.12 mole) is added, and the mixture is heated at 135° C. for 6 hours.

The mixture is then cooled to 90° C. and to it 40%-concentrated potassium hydroxide (30 ml) is added, and the mixture is then kept at the temperature said for 5 hours. The mixture is then processed as described in preceding Examples.

2-(6'-Methoxy-naphthyl)-propionic acid is obtained (10.5 g; 0.456 mole).

Yield of 45%; melting point, 154°-155° C.

EXAMPLE 4

Preparation of 2-(4'-isobutylphenyl)-propionic acid

A mixture of 2-bromo-4'-isobutylpropiophenone (35.1 g; 0.130 mole), 2,2-dimethyl-1,3-propanediol (31.35 g; 0.3 mole), and p-toluenesulphonic acid (1.9 g; 0.01 mole) in toluene (109) is refluxed for 6 hours, while azeotropically distilling off the developing water by means of an equipment provided with suitable fraction separation unit (fiorentina).

From the mixture neutralized with sodium methoxide (0,6 g; 0.011 mole) the toluene is withdrawn by vacuum distillation. Ethylene glycol (140 g) and potassium acetate (14.7 g; 0.15 mole) is then added, and the mixture is heated at 135° C. for 5 hours.

To the solution thus obtained, cooled to 90° C., a 40% aqueous solution of sodium hydroxide (130 g) is added, and the whole is heated at 110° C. for 2 hours.

The reaction mixture is then cooled to room temperature, poured into water (150 ml), and extracted with methylene chloride (3×100 ml).

From the water phase, by making it acid to pH 1 by means of concentrated hydrochloric acid, 2-(4'-isobutylphenyl)propionic acid precipitates (19.1 g; 0.093 mole), melting point 75°-76° C. Yield of 72%.

EXAMPLE 5

Preparation of 2-(2'-thienyl)-propionic acid

A mixture of 2-bromo-1-(2'-thienyl)-propan-1-one (20,5 g; 0.094 mole) (prepared following Doklady Akad Naysk SSSR, 138, 115 [1961]), 2,2-dimethyl-1,3-propanediol (19.24 g; 0,185 mole) and p-toluenesulphonic acid monohydrate (0.932 g; 0.0049 mole) in xylene (47 ml) is refluxed for 6 hours, while azeotropically distilling off developing water by means of an equipment provided with a suitable fraction separating unit (fiorentina).

The mixture is neutralized with sodium methoxide (0.269 g; 0.0049 mole). After having withdrawn the toluene by vacuum distillation, ethylene glycol (32.5 g; 0.52 mole), 2,2-dimethyl-1,3-propanediol (13.75 g; 0.13 mole) and potassium acetate (10.25 g; 0.11 mole) is added, and the mixture is heated at 150° C. for 5 hours.

The solution so obtained is cooled to room temperature, and processed as in preceding Examples.

The residue is vacuum distilled; 2-(2'-thienyl)-propionic acid is thus obtained (boiling point 98°-100° C./0.5 mmHg) (11.7 g; 0.075 mole) (yield of 80%).

We claim:

1. A process for preparing an alpha-aryl-alkanoic acid comprising heating a mixture of a corresponding alpha-bromo- or chloro-alkyl-aryl-ketone in (a) a saturated straight or branched chain aliphatic diol, or (b) a mixture thereof, said saturated diol having from 2 to 10 carbon atoms, in the presence of a Broensted's acid, and subsequently making the resulting reaction mixture alkaline.

2. The process of claim 1 wherein the reaction is carried out at the boiling temperature of the reaction mixture.

3. The process of claim 1 which includes distilling off a mixture of water and diol during said heating operation and reintegrating said water-diol mixture into said reaction mixture, as said water-diol distills, with an equal amount of fresh diol.

4. The process of claim 1 wherein the reaction mixture is heated at the boiling temperature thereof for 2-30 hours.

5. The process of claim 1 wherein prior to making the reaction mixture alkaline, the temperature of the reaction mixture is adjusted to a temperature ranging from 60° to 100° C. and wherein subsequent to making the reaction mixture alkaline, the reaction mixture is maintained at said temperature for 3-7 hours.

* * * * *